(12) United States Patent
Noe' et al.

(10) Patent No.: US 8,198,439 B2
(45) Date of Patent: Jun. 12, 2012

(54) PROCESS FOR THE PURIFICATION OF MELAMINE AND RELATIVE EQUIPMENT

(75) Inventors: Sergio Noe', San Donato Milanese (IT); Roberto Santucci, Gorla Maggiore (IT)

(73) Assignee: EUROTECNICA MELAMINE, LUXEMBOURG, Zweigniederlassugn in Ittigen, Ittigen (CH)

( * ) Notice: Subject to any disclaimer, the term of this patent is extended or adjusted under 35 U.S.C. 154(b) by 375 days.

(21) Appl. No.: 12/465,177

(22) Filed: May 13, 2009

(65) Prior Publication Data

US 2009/0286979 A1 Nov. 19, 2009

(30) Foreign Application Priority Data

May 13, 2008 (IT) .............................. MI2008A0861

(51) Int. Cl.
*C07D 251/60* (2006.01)
*C07D 251/62* (2006.01)
(52) U.S. Cl. ...................... 544/203; 544/201
(58) Field of Classification Search .................. 544/293, 544/201, 203
See application file for complete search history.

(56) References Cited

U.S. PATENT DOCUMENTS

| 3,161,638 | A | * | 12/1964 | Christoffel | 544/203 |
|---|---|---|---|---|---|
| 3,296,266 | A | | 1/1967 | Nelson et al. | |
| 3,637,686 | A | * | 1/1972 | Kokubo et al. | 544/203 |
| 4,408,046 | A | * | 10/1983 | Van Hardeveld | 544/201 |
| 5,721,363 | A | | 2/1998 | Canzi et al. | |
| 6,774,234 | B1 | | 8/2004 | Noe | |
| 7,153,962 | B1 | | 12/2006 | Ripperger | |
| 2008/0275234 | A1 | | 11/2008 | Ruech | |

FOREIGN PATENT DOCUMENTS

| GB | 958633 | 5/1964 |
|---|---|---|
| WO | 01/36397 | 5/2001 |
| WO | 02/100839 | 12/2002 |

\* cited by examiner

*Primary Examiner* — Venkataraman Balasubramanian
(74) *Attorney, Agent, or Firm* — Oblon, Spivak, McClelland, Maier & Neustadt, L.L.P.

(57) ABSTRACT

The present invention relates to an improved process for the purification of melamine obtained by synthesis from urea which comprises the following steps: a) bringing raw melamine containing impurities of polycondensates and other by-products of the synthesis reaction, into solution, obtaining a solution/suspension in which the insoluble products are dispersed; b) subjecting the solution/suspension thus obtained to treatment to remove the $CO_2$ dissolved, reducing its concentration to values lower than 0.5% by weight; c) treating the solution/suspension obtained in step b), having a content of $CO_2$ lower than 0.5% by weight, with ammonia in a quantity ranging from 1 to 15%, preferably from 3 to 9% by weight, at a temperature ranging from 110 to 180° C., preferably from 130 to 140° C.; d) putting the solution leaving step c) in contact with a solid catalyst, under the same conditions as step c). The present invention also relates to the equipment for effecting said process.

15 Claims, No Drawings

PROCESS FOR THE PURIFICATION OF MELAMINE AND RELATIVE EQUIPMENT

The present invention relates to an improved process for the purification of melamine and the relative equipment.

In particular, the present invention relates to a process for the purification of melamine produced by synthesis from urea and more specifically a process which allows a part of the impurities formed in the synthesis or during the subsequent manipulations of melamine, to be reconverted into melamine.

It is known, in fact, that in the synthesis of melamine from urea, intermediate reaction by-products are formed which influence the purity of the melamine. The most important among these intermediate reaction products are ammeline and ammelide, normally indicated as oxyaminotriazines (OATs), whose presence in the product in quantities higher than 500-1,000 ppm is harmful for the subsequent formation of resins based on melamine-formaldehyde.

In addition to OATs, during the reaction and downstream of this, under particular conditions of reduced partial ammonia pressure, another category of by-products is formed due to the condensation reaction of various melamine molecules with each other and the consequent release of one or more ammonia molecules. These by-products are known under the collective name of polycondensates. Examples of polycondensates are melam and melem, to mention only the most common of these, characterized by the following molecular structures:

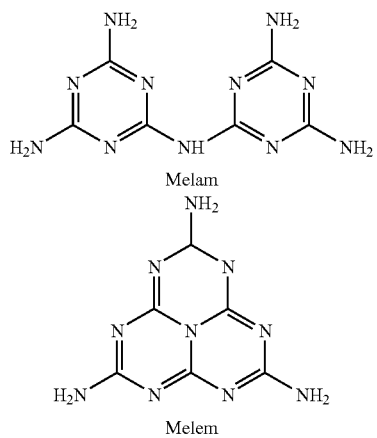

The lower the partial ammonia pressure, the higher the temperature and the higher the residence time of the melamine under the above conditions, the higher the formation of polycondensates will be.

Like OATs, also these products are harmful for the subsequent use of melamine in the formation of resins by condensation with formaldehyde. A level of polycondensates lower than 1,000 ppm in the end-product represents an acceptability limit of the product.

The reactions which lead to the formation of polycondensates are reversible. Melamine polluted with polycondensates can therefore be purified by subjecting it to the prolonged action of ammonia, under adequate temperature and partial pressure conditions. Due to the action of ammonia, not only are the polycondensates eliminated, but, as these are transformed back into melamine, a recovery of the overall process yield is also obtained.

The operating conditions which allow this objective to be reached, however, are extremely onerous economically, as they require the treatment of molten melamine at partial ammonia pressures higher than 250 bars, preferably higher than 400 bars, to obtain a melamine having an acceptable purity.

The transformation conditions of polycondensates in an aqueous ammonia environment, on the other hand, are blander and economically more favourable.

Most of the melamine synthesis processes which are industrially operating include the recovery, in an aqueous medium, of the raw melamine leaving the synthesis reactor. The process consists of feeding the reaction product, consisting of a liquid phase, raw melamine, and a gaseous phase mainly consisting of $NH_3$ and $CO_2$, into a suitable contact apparatus (Quench tower, or simply Quench) in which said reaction product is cooled in the presence of water in which the raw melamine dissolves, together with part of the gaseous phase. At the same time, the pressure is reduced from the reaction pressure (over 70 bar) to a pressure normally lower than 25 bar, corresponding to a thermodynamic equilibrium temperature lower than 165° C. in order to limit corrosion phenomena.

A gaseous phase containing $NH_3$, $CO_2$ and water vapour is then formed following this operation, together with a liquid aqueous phase containing, in solution, in addition to $NH_3$ and $CO_2$ corresponding to the thermodynamic equilibrium, melamine, OATs, polycondensates, non-reacted urea and other minor impurities. The melamine content in the liquid phase can vary from 5 to 15% by weight, whereas the OATs are present within the range of 0.1-0.4% by weight. In particular, polycondensates are present in the aqueous solution in a ratio ranging from 1:30 to 1:60 by weight with respect to the melamine and their physical state (solution or suspension) depends on the particular temperature conditions and ammonia concentration adopted.

By subjecting the solution/suspension leaving the Quench to the action of ammonia, the polycondensates are transformed into melamine. The higher the concentration of $CO_2$ in the liquid phase, the slower this transformation will be, thus requiring very high contact times to reach a transformation degree of polycondensates compatible with the specific purity requirements of the melamine.

For this purpose, in industrial practice, the above solution/suspension is subjected, with or without the addition of further ammonia, to treatment at a temperature normally lower than 165° C. for a sufficient time which varies from one to several hours. This operation requires considerable volumes for the treatment, which, due to the temperature and pressure conditions and the nature of the material subjected to the treatment, requires the use of particular stainless steels, sheets having a considerable thickness and therefore high costs. During this treatment, there is also an undesired loss of product due to the contemporaneous hydrolysis reaction of melamine with water and the formation of OATs. The higher the temperature and the longer the treatment requested for the reduction of the polycondensates, the greater this loss will be.

An improved process for the removal of polycondensates present as impurities in the melamine produced by the pyrolysis of urea is described in U.S. Pat. No. 6,774,234 (US'234) of the same Applicant.

The process includes the dissolution of raw melamine in an aqueous environment in the Quench apparatus, the subsequent removal of $CO_2$ to a concentration lower than 0.5% by weight followed by reaction with ammonia added in a quantity of 5-25% by weight, at a temperature ranging from 100 to 250° C. for a few minutes. A solution is recovered from the above treatment having a concentration of polycondensates lower than 1,000 ppm, typically lower than 100 ppm, from which the melamine can then be crystallized.

Even if the present state of the art is capable of purifying melamine from OATs and polycondensates at acceptable levels, there is the necessity of operating at high concentrations of ammonia and relatively high temperatures with consequent high investment costs and energy consumption.

The present invention has the objective of solving the above-mentioned problems in the purification of melamine.

A first object of the present invention therefore relates to an improved process for the purification of melamine obtained by synthesis from urea, comprising the following steps:
a) bringing raw melamine containing impurities of polycondensates and other by-products of the synthesis reaction, into solution, obtaining a solution/suspension in which the insoluble products are dispersed;
b) subjecting the solution/suspension thus obtained to treatment to remove the $CO_2$ dissolved, reducing its concentration to values lower than 0.5% by weight;
c) treating the solution/suspension obtained in step b), having a content of $CO_2$ lower than 0.5% by weight, with ammonia in a quantity ranging from 1 to 15%, preferably from 3 to 9% by weight, at a temperature ranging from 110 to 180° C., preferably from 130 to 140° C.;
d) putting the solution leaving step c) in contact with a solid catalyst, under the same conditions as step c).

At the end of step d) the concentration of polycondensates in the melamine solution is reduced to values lower than 100 ppm by weight.

The Applicant has surprisingly found that it is possible to overcome the drawbacks observed in the state of the art, by subjecting the melamine solution/suspension to a digestion treatment with $NH_3$, under much blander conditions with respect to those envisaged in US'234, following the above treatment with a finishing phase on a solid catalytic carrier operating under unchanged conditions of temperature and $NH_3$ concentration. In particular, it has been observed that the combination of the above two treatments (digestion and finishing), under suitable conditions, allows the reduction of polycondensates in the solution/suspension to values lower than 100 ppm, operating at a lower temperature with respect to the known processes of the art, thus also reducing the formation of OATs. Melamine having a high purity can be obtained from the solution thus purified, by crystallization and subsequent drying, with considerable advantages in terms of costs and consumptions.

In step a) of the process, the raw melamine is brought into solution, i.e. is dissolved in water. The melamine contains impurities of polycondensates and other by-products of the synthesis reaction, which can remain in suspension as they have a low solubility.

The reduction of the $CO_2$ content in step b) is preferably obtained by stripping with an inert gas, wherein inert gas means a gas which is inert with respect to the components of the solution/suspension. The gas used for the stripping of the solution/suspension is preferably water vapour. By subjecting the raw melamine solution/suspension coming from the Quench to a vapour stripping operation, the $NH_3$ and $CO_2$ dissolved therein are almost completely eliminated. The operation is effected so as to lower the $CO_2$ residual concentration in the melamine solution/suspension to a value lower than 0.5% by weight.

Ammonia is added to said decarbonated raw melamine solution/suspension in a quantity of 1-15% by weight, preferably 3-9% by weight, at a temperature of 110-180° C., preferably at a temperature of 130-140° C. and at the corresponding equilibrium pressure. By maintaining the system under these conditions for a time of between 10 and 30 minutes, preferably less than 15 minutes, the polycondensates present in the original solution/suspension are converted into melamine for over 70% of their original value.

A fundamental phase of the process according to the present invention is step d) i.e. the finishing treatment in which the solution leaving step c) is put in contact with a solid catalyst under the same conditions as step c). Step d) is preferably effected with a solid catalyst consisting of a bed of activated carbon. Although this finishing step is aimed at completing the transformation of the polycondensates which remain from the digestion treatment with ammonia, it is capable of also removing other possible impurities, soluble and/or insoluble, present in the solution with an improvement in the final colour of the product.

The total transformation of the polycondensates on the solid catalyst, in particular on activated carbon, can be preceded by a mechanical filtration step aimed at withholding other possible insoluble impurities present in the solution leaving the above-mentioned step c). If present, the mechanical filtration step helps to prevent or at least slow down the possible deactivation of the solid catalyst bed, preferably activated carbon, due to pure mechanical blockage.

The process according to the present invention can also comprise a second mechanical filtration step of the solution containing melamine, downstream of the finishing treatment on the activated carbon bed, in order to withhold and remove any possible solid impurities still present, comprising catalyst residues.

A further object of the present invention relates to equipment for effecting the melamine purification process, comprising:
a column for the treatment with ammonia in liquid phase of a solution/suspension of raw melamine containing impurities of polycondensates and other by-products of the synthesis reaction of melamine;
a catalytic bed for completing the transformation of the residual polycondensates present in the solution/suspension of raw melamine leaving the column for treatment with ammonia.

The column for the treatment with ammonia of the solution/suspension of raw melamine containing impurities of polycondensates and other by-products of the synthesis reaction can consist of a conventional tower having a height/diameter ratio higher than 2.

The catalytic bed with which the solution/suspension of raw melamine is put in contact in the finishing phase of the purification process is preferably a bed of activated carbon.

In a preferred embodiment, the equipment also comprises mechanical filtration means for removing the impurities remaining in suspension in the solution leaving the treatment column with ammonia. These means, for example a bed of solid inert material, are positioned upstream of the catalytic bed and are functionally connected to the column from which they receive the solution treated with ammonia. The mechanical filtration of the solution not only purifies the melamine by withholding the insoluble solid impurities, but also contributes to preventing blockages of the catalytic bed and consequently delaying its deactivation.

The equipment can also comprise further mechanical separation means (guard filter) functionally connected to the catalytic bed from which they receive the solution containing melamine in order to withhold any possible solid impurities still present after the treatment on the catalytic bed, comprising possible catalyst residues.

With respect to the known processes in the state of the art, the process according to the present invention and the relative equipment for effecting it, allow impurities of polycondensates to be eliminated from the aqueous solution containing the melamine to be crystallized, in a conveniently short time (less than 40 minutes) and with a reduced consumption of $NH_3$, with a consequent saving of vapour for its recovery in the subsequent phases of the melamine production process.

The process conditions for the purification of melamine, which are much blander than those of the known purification processes, also lead to an increase in the overall yield of the melamine production process, as it is possible to operate at much lower treatment temperatures with respect to those of the present state of the art. Under the optimum treatment conditions, in fact, the formation of OATs by the hydrolysis of melamine is considerably reduced.

Some application examples are provided for a better illustration of the objectives and advantages of the present invention but they should in no way be considered as representing a limitation of the scope of the claims.

EXAMPLE 1

A solution leaving the Quench and having the following composition (by weight):

| | |
|---|---|
| $H_2O$ | 68.5% |
| Melamine | 10% |
| OATs | 0.3% |
| Polycondensates | 0.23% |
| Urea | 0.47% |
| $NH_3$ | 16.7% |
| $CO_2$ | 3.8% | was subjected to stripping with vapour effected at 5 bar and at 160° C. (column bottom values), allowing a decarbonated solution having the following composition (again by weight) to be obtained:

| | |
|---|---|
| $H_2O$ | 88.7% |
| Melamine | 9.5% |
| OATs | 0.32% |
| Polycondensates | 0.24% |
| Urea | 0.4% |
| $NH_3$ | 0.51% |
| $CO_2$ | 0.33%. |

A quantity of ammonia equal to 4% by weight was added to this solution, contemporaneously lowering the temperature to a value of 140° C. The solution was then fed to the equipment according to the present invention comprising in succession: a column for treatment with $NH_3$, a mechanical filtration device, a bed of activated carbon and finally a guard filter. In the treatment phase with $NH_3$, the solution containing melamine is left to stand inside the column for 15 minutes. The first mechanical filtration, the finishing treatment on the bed of activated carbon and the filtration by means of the guard filter were effected maintaining the solution containing melamine under the same conditions of temperature and ammonia concentration as the treatment column with ammonia. The finishing step on activated carbon and filtration envisaged the residence of the melamine under the above conditions for an additional 20 minutes.

At the outlet of the equipment, the total disappearance of the polycondensates is observed, their concentration being below the analytical limit of the detection method used (Ultraviolet spectrophotometry) and therefore below 10 ppm.

Due to the residence of the aqueous solution under conditions of 140° C. in the presence of 4% by weight of $NH_3$ for the time indicated, the melamine undergoes the hydrolysis reaction which brings the value of the OATs from the initial 33,300 ppm to the final 43,300 ppm with respect to the melamine. During the treatment, a loss of melamine due to hydrolysis equal to 1% by weight is therefore registered.

The recovery of the ammonia added to reach the 4% by weight required by the treatment, which is effected on the crystallization mother liquor, requires a vapour consumption equal to 4,260 Kg for each ton of melamine produced.

The colour of the melamine crystallized and dried according to the known methods of the art proves to be lower than the value of 10 according to the APHA scale.

EXAMPLE 2 (COMPARATIVE)

The decarbonated solution of Example 1 was treated according to what is described in patent US'234. Ammonia was added to the solution up to a concentration of 13% by weight approximately and then fed to a suitable column for treatment with ammonia at a pressure of 25 bar and a temperature of 172° C.

The residence time in this column was a further 15 minutes approximately and the concentration of polycondensates at the outlet of the column proved to be lower than the analytical limit of the detection method used (Ultraviolet spectrophotometry) (i.e. lower than 10 ppm).

The solution leaving the above treatment column was then subjected to normal bleaching treatment which envisaged a further residence time of 15 minutes for the complete elimination of the impurities in suspension and to ensure the formation of a product having an APHA colour value below 20.

Under the treatment conditions described in US'234, a hydrolysis degree of the melamine to OATs equal to 1.7% by weight is observed, with a greater loss of product equal to 70% with respect to that corresponding to the process according to the present invention.

Furthermore, the recovery of the $NH_3$ necessary for the treatment (amounting to about 13% by weight) from the crystallization mother liquor requires a vapour consumption of 4,930 Kg per ton of melamine, i.e. a greater consumption of 0.67 tons of vapour per ton of melamine produced, with respect to the consumption corresponding to the treatment claimed by the invention.

The invention claimed is:

1. An improved process for the purification of melamine obtained by synthesis from urea, comprising:
   a) bringing raw melamine containing impurities of polycondensates and other by-products of the synthesis reaction, into solution, obtaining a solution/suspension in which the insoluble products are dispersed;
   b) subjecting the solution/suspension thus obtained to treatment to remove the $CO_2$ dissolved, reducing its concentration to values lower than 0.5% by weight;
   c) treating the solution/suspension obtained in step b), having a content of $CO_2$ lower than 0.5% by weight, with ammonia in a quantity ranging from 1 to 4% at a temperature ranging from 110 to 180° C.;
   putting the solution leaving step c) in contact with a solid catalyst, under the same conditions as step c).

2. The process according to claim 1, wherein the solid catalyst is a bed of activated carbon.

3. The process according to claim 1, wherein phase b) for the removal of the $CO_2$ dissolved is effected by stripping with an inert gas.

4. The process according to claim 1, further comprising a mechanical filtration of the solution leaving step c), before the treatment of step d).

5. The process according to claim 1, further comprising a mechanical filtration of the solution leaving d).

6. The process according to claim 1, wherein the solution leaving d) has a concentration of polycondensates lower than 100 ppm by weight.

7. The process according to claim 1, wherein the solution/suspension obtained in b) is treated at a temperature of from 130 to 140° C.

8. The process according to claim 3, wherein the inert gas is water vapor.

9. The process according to claim 1, wherein during the treating (c) the amount of melamine hydrolyzed to form oxyaminotriazines is less than 1% by weight.

10. The process according to claim 1, wherein the treating (c) is carried out in a column.

11. The process according to claim 1, wherein the contacting after the treating (c) eliminates melamine polycondensates from the solution/suspension.

12. The process according to claim 1, wherein the treating (c) converts over 70% of melamine polycondensates present in the solution/suspension into melamine.

13. The process according to claim 1, wherein the treating (c) is carried out at a temperature of 110-130° C.

14. A process for purifying a melamine-containing composition, comprising:
(a) dissolving the melamine composition in water to form a first melamine solution comprising melamine, one or more melamine polycondensates and one or more by-products;
(b) reducing the concentration of $CO_2$ in the first melamine solution to an amount of lower than 0.5% by weight to form a reduced-$CO_2$ melamine solution;
(c) treating the reduced-$CO_2$ melamine solution with ammonia in an amount of from 1 to 9% by weight at a temperature of from 130 to 140° C. to form a melamine-ammonia solution;
(d) contacting the melamine-ammonia solution formed in (c) with an activated carbon bed;
wherein the treating (c) converts over 70% of the melamine polycondensates to melamine, and the contacting (d) eliminates melamine polycondensates from the melamine-ammonia solution.

15. The process according to claim 14, wherein the loss of melamine due to hydolysis to form oxyaminotriazine is less than 1% by weight.

* * * * *